(12) United States Patent
Scott et al.

(10) Patent No.: US 9,927,049 B1
(45) Date of Patent: Mar. 27, 2018

(54) TUBE HANGERS AND SYSTEMS FOR VERY EARLY SMOKE DETECTION

(71) Applicant: THE BOEING COMPANY, Chicago, IL (US)

(72) Inventors: Matthew Lee Scott, Charleston, SC (US); Derek James Carr, Ladson, SC (US); Nathan A. Brian, Summerville, SC (US); Andrew M. Huckey, Charleston, SC (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/483,385

(22) Filed: Apr. 10, 2017

(51) Int. Cl.
| | | |
|---|---|---|
| *G01N 21/00* | (2006.01) | |
| *F16L 3/127* | (2006.01) | |
| *F16B 45/00* | (2006.01) | |
| *G01N 21/53* | (2006.01) | |
| *G08B 17/107* | (2006.01) | |
| *H04B 5/00* | (2006.01) | |

(52) U.S. Cl.
CPC .............. *F16L 3/127* (2013.01); *F16B 45/00* (2013.01); *G01N 21/53* (2013.01); *G08B 17/107* (2013.01); *H04B 5/0062* (2013.01)

(58) Field of Classification Search
CPC ....... F16L 3/00; F16L 3/08; F16L 3/12; F16L 3/13; F16L 3/24; F16L 3/127; F16B 45/00; G01N 21/53; G08B 17/107; H04B 5/0062; A21C 13/00; A21C 13/02; A21C 9/02; A21C 9/00; G02B 21/06; F21V 25/00; A61B 19/00; E21F 17/02; F16M 13/00; E05B 73/00
See application file for complete search history.

(56) References Cited

U.S. PATENT DOCUMENTS

| | | | |
|---|---|---|---|
| 4,042,198 A | 8/1977 | Takeuchi | |
| 5,385,320 A * | 1/1995 | Ismert | F16L 3/10 248/62 |
| 2014/0192224 A1 | 7/2014 | Ruh et al. | |

\* cited by examiner

*Primary Examiner* — Jamil Ahmed
(74) *Attorney, Agent, or Firm* — Armstrong Teasdale LLP

(57) ABSTRACT

A tube hanger for a very early smoke detection system is provided. The tube hanger includes a tube hook configured to receive a tube, a suspension arm having a first end extending from the tube hook and a second end, and a support coupling mechanism extending from the second end of the suspension arm. The support coupling mechanism includes a first attachment mechanism configured to be coupled to a first frame type, and a second attachment mechanism configured to be coupled to a second frame type. The tube hanger further includes a third attachment mechanism extending from the support coupling mechanism and configured to be coupled to a third frame type.

20 Claims, 7 Drawing Sheets

TUBE HANGERS AND SYSTEMS FOR VERY EARLY SMOKE DETECTION

BACKGROUND

The field of the disclosure relates generally to tube hangers and, more specifically, to tube hangers and systems for very early smoke detection.

A very early smoke detection apparatus (VESDA) uses aspirating smoke detection to sense small amounts of smoke in an environment, typically far smaller amounts than can be noticed visually. Such very early smoke detection is useful in a variety of applications, especially where the environment is isolated, large, and/or contains high value assets. For example, very early smoke detection may be useful during the manufacture of large, complex apparatuses such as aircrafts. During manufacturing of aircrafts, including during construction, repair, maintenance, retrofitting, and/or interior finishing, a VESDA may be temporarily installed in the (at least partially assembled) aircraft.

A VESDA detects smoke, and potentially other hazard indicators, by sampling the air in an environment. A VESDA system includes a monitoring device and tubing (e.g., piping, conduit, ducting, and/or hose) distributed about the area to be protected. The tubing typically includes a series of sampling inlets that are configured to draw air from the local environment through the tubing to the monitoring device. The monitoring device receives the air, optionally filters the air, and for smoke detection applications, measures remaining particulates by light scattering.

The tubing is typically coupled to the interior of the aircraft. One known method of mounting the tubing includes using zip ties or similar fasteners to couple the tubing to a portion of the aircraft. However, the use of zip ties may lead to foreign object debris, inconsistent installation, and/or installation on aircraft components that may cause damage to the VESDA and/or the aircraft component. Additionally, as various stages of the aircraft manufacturing process are completed, the tubing needs to be moved so personnel can access certain areas within the aircraft. Because the zip ties are not conveniently removable and replaceable, the tubing often gets laid on the floor. This creates safety hazards for personnel, including a trip hazard for those trying to maneuver through the aircraft and a fire hazard as the tubing is not installed in the proper location to detect smoke. Moreover, the VESDA tubing may get damaged and is very costly to replace.

Another known method of mounting the tubing includes using tube hangers. However, such tube hangers are typically configured for installation in a specific aircraft and/or for coupling to a specific component within the aircraft. Thus, the lack of versatility of aircraft components to which such mount apparatuses may be attached may also result in improper installation of the tubing.

BRIEF DESCRIPTION

According to one aspect of the present disclosure, a tube hanger for a very early smoke detection system is provided. The tube hanger includes a tube hook configured to receive a tube, a suspension arm having a first end extending from the tube hook and a second end, and a support coupling mechanism extending from the second end of the suspension arm. The support coupling mechanism includes a first attachment mechanism configured to be coupled to a first frame type, and a second attachment mechanism configured to be coupled to a second frame type. The tube hanger further includes a third attachment mechanism extending from the support coupling mechanism and configured to be coupled to a third frame type.

According to another aspect of the present disclosure, a tube hanger for a very early smoke detection system is provided. The tube hanger includes a tube hook configured to receive a tube, a support coupling mechanism including a first attachment mechanism configured to be coupled to a first frame type during a first stage of manufacturing of a vehicle, and a second attachment mechanism configured to be coupled to a second frame type during a second stage of manufacturing of the vehicle. The tube hanger also includes a third attachment mechanism extending from the support coupling mechanism and configured to be coupled to a third frame type during a third stage of manufacturing of the vehicle. The tube hanger further includes a suspension arm spanning between the tube hook and the support coupling mechanism.

According to yet another aspect of the present disclosure, a very early smoke detection system is provided. The system includes a monitoring device, a sampling tube coupled to the monitoring device, and a tube hanger for mounting the sampling tube in an environment. The tube hanger includes a tube hook configured to receive the sampling tube, a suspension arm having a first end extending from the tube hook and a second end, and a support coupling mechanism extending from the second end of the suspension arm. The support coupling mechanism includes a first attachment mechanism configured to be coupled to a first frame type, and a second attachment mechanism configured to be coupled to a second frame type. The tube hanger further includes a third attachment mechanism extending from the support coupling mechanism and configured to be coupled to a third frame type.

The features, functions, and advantages that have been discussed can be achieved independently in various embodiments or may be combined in yet other embodiments further details of which can be seen with reference to the following description and drawings.

DETAILED DESCRIPTION

As used herein, an element or step recited in the singular and proceeded with the word "a" or "an" should be understood as not excluding plural elements or steps unless such exclusion is explicitly recited. Furthermore, references to "one embodiment" of the present invention or the "exemplary embodiment" are not intended to be interpreted as excluding the existence of additional embodiments that also incorporate the recited features.

Figure 1:
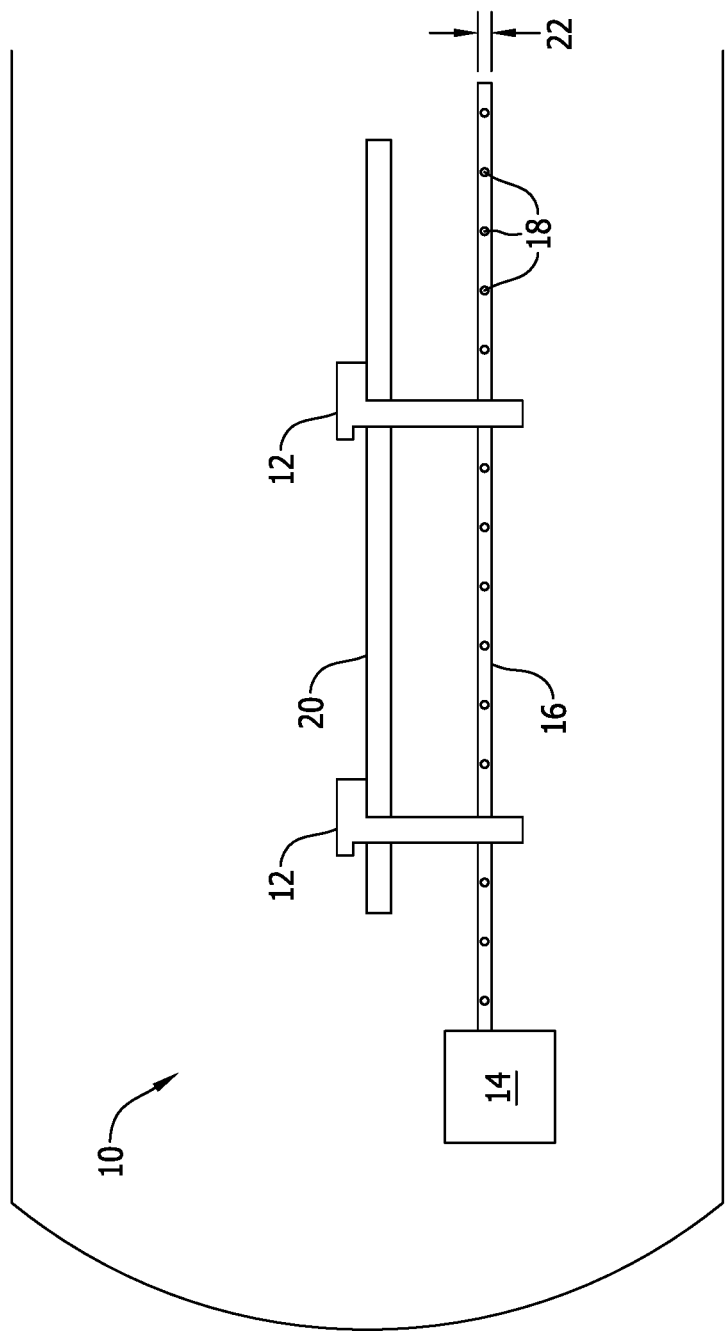
FIG. 1 is a schematic representation of a system for very early smoke detection that includes a tube hanger.

FIG. 1 is a schematic representation of a system 10 for very early smoke detection that includes a tube hanger 12. System 10 also includes a monitoring device 14, and one or more sampling tubes 16. Generally, system 10 is configured to detect smoke from an environment by aspirating air samples through a sampling tube 16 and delivering those air samples to the monitoring device 14 where smoke may be detected. Tube hangers 12 are configured to couple sampling tubes 16 to support structures 20, structures that are within, or at least partially define, a monitored region of the environment. Sampling tubes 16 in system 10 are arranged to sample air generally throughout the monitored region. System 10 is configured for use during manufacture of aircrafts, including during construction, repair, maintenance, retrofitting, and/or interior finishing. System 10 is configured for temporary installation. For example, system 10 is configured for installation in an aircraft during interior finishing and for removal from the aircraft after completion of manufacture.

Sampling tube 16, typically a network of sampling tubes 16, includes at least one sampling inlet 18 for sampling air from the neighboring environment. Sampling tube 16 is configured to channel the sampled air to monitoring device 14. Sampling tube 16 may include pipe, conduit, ductwork, and/or hose. Further, sampling tube 16 may include at least a portion that is flexible or rigid. Sampling tube 16 is characterized by an outer diameter 22. The outer diameter 22 is the effective diameter of the outer profile of sampling tube 16 (i.e., sampling tube 16 need not have a circular profile.

Tube hanger 12 is configured to couple a portion of sampling tube 16 to a support structure 20. Support structure 20 may be a portion or a component of an aircraft, for example, a portion of an aircraft interior such as a side/overhead rail or a stowage bin in an aircraft cabin. Tube hanger 12 is configured to be easily coupled to and removed from multiple types of support structures 20 so that personnel working on the aircraft always have a convenient location to couple tube hanger 12 to, regardless of the stage of manufacturing.

Monitoring device 14 is configured to detect the presence of smoke in the sampled air delivered by sampling tube 16. Additionally or alternatively, monitoring device 14 may detect other properties of the sampled air, for example, temperature, moisture, and/or hazardous gases. Generally, monitoring device 14 is detects smoke by measuring light scattering (the presence of smoke causes light to scatter as light is transmitted through a sample of air). Monitoring device 14 is configured to draw air through sampling tube 16, and thereby aspirate samples of air from the environment. In some implementations, monitoring device 14 includes a suction device configured to draw air through sampling tube 16 towards monitoring device 14.

Figure 2:
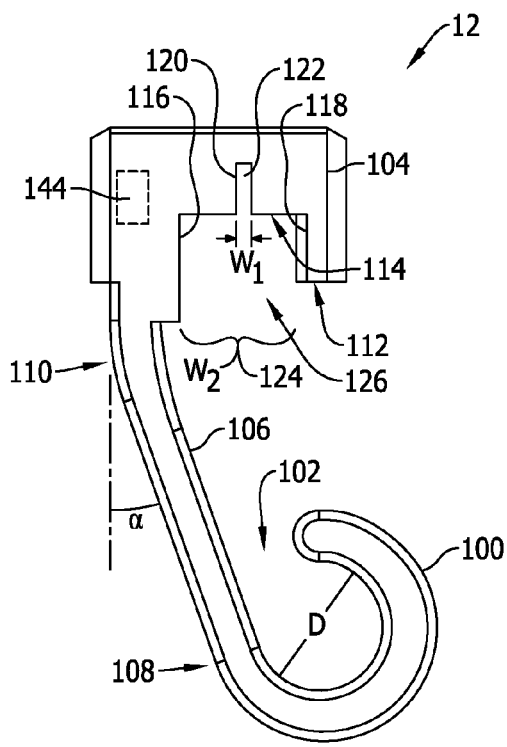
FIG. 2 is a side view of the tube hanger shown in FIG. 1.
Figure 3:
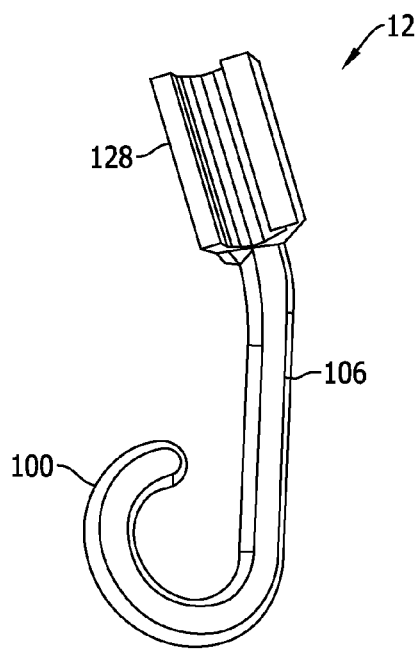
FIG. 3 is a perspective view of the tube hanger shown in FIGS. 1 and 2.
Figure 4:
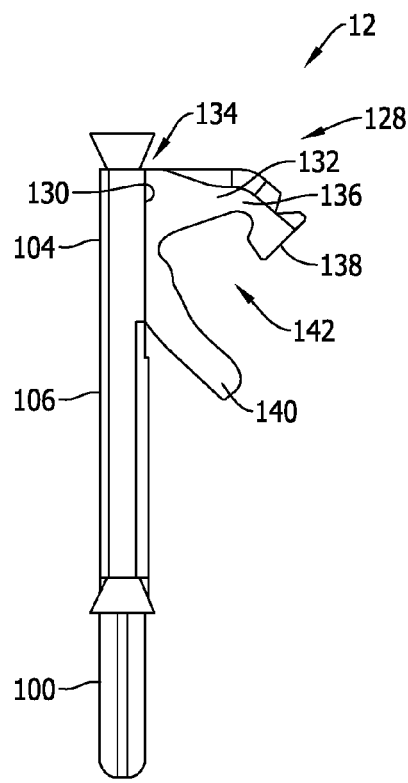
FIG. 4 is a top view of the tube hanger shown in FIGS. 1-3.
Figure 5:
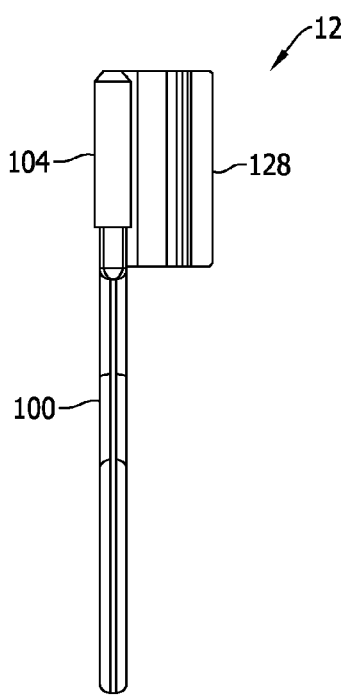
FIG. 5 is a rear view of the tube hanger shown in FIGS. 1-4.

FIG. 2 is a side view of tube hanger 12 (shown in FIG. 1). FIG. 3 is a perspective view of tube hanger 12. FIG. 4 is a top view of tube hanger 12. FIG. 5 is a rear view of tube hanger 12.

Tube hanger 12 includes a tube hook 100 defining a hook opening 102, a support coupling mechanism 104, and a suspension arm 106 spanning between tube hook 100 and support coupling mechanism 104. Tube hanger 12 is configured for at least temporary coupling to one or more support structures 20. That is, tube hanger 12 is configured to be coupled to and uncoupled from one or more support structures 20 within the aircraft. Tube hanger 12 is configured to be coupled to and uncoupled from support structures 20 repeatedly without damaging support structure 20 and/or tube hanger 12. A plurality of tube hangers 12 may be used to couple sampling tube 16 to support structure 20 over an extended length of support structure 20.

Tube hook 100 defines hook opening 102, which faces upward, towards support coupling mechanism 104. Tube hook 100 is configured to receive and to retain sampling tube 16. Tube hook 100 is configured to accept sampling tube 16 via hook opening 102. Sampling tube 16 may be inserted into tube hook 100 laterally (along the tubing elongate direction) and/or transversely (generally perpendicularly to the tubing elongate direction) through hook opening 102. In some implementations, when sampling tube 16 is inserted, tube hook 100 generally elastically flexes, stretches, and/or expands to accommodate sampling tube 16.

Tube hook 100 is circular over an arc of more than 180° and less than 360°. Because hook opening 102 faces upward, tube hook 100 is biased to retain sampling tube 16 using either a loose fit or a friction fit. That is, tube hook 100 has an inner diameter D that is greater than or equal to outer diameter 22 of sampling tube 16. Hook opening 102 is oriented to face generally upward, towards support coupling mechanism 104 and support structure 20 (when tube hanger 12 is installed). Hook opening 102 may be described as an opening, an aperture, a gap, a slit, a slot, and/or a cleft.

Suspension arm 106 includes a first end 108 extending from tube hook 100 and a second end 110 extending from support coupling mechanism 104, such that support coupling mechanism 104 is positioned relatively vertically above tube hook 100. Suspension arm 106 is flexible and/or has an arcuate profile. That is, suspension arm 106 extends from support coupling mechanism 104 at an angle α relative to the vertical direction. When installed, angle α of suspension arm 106 enables tube hanger 12 to retain sampling tube 16 substantially directly below the support structure 20 and at a distance away from support structure 20. Holding sampling tube 16 away from support structure 20 enables access to support structure 20 near sampling tube 16 and/or enables system 10 to better sample the environment by providing air access around sampling tube 16.

Support coupling mechanism 104 is configured to couple tube hanger 12 to support structure 20. Support structure 20 may include a frame, a rail, a rib, a flange, ducting, a stowage bin, and/or an air outlet. Support coupling mechanism 104 may be configured to couple to a range of sizes and/or types of support structures 20.

Support coupling mechanism 104 includes a bottom surface 112. At least a portion of bottom surface 112 is a recessed bottom surface 114 that is recessed within support coupling mechanism 104. First and second recessed side surfaces 116 and 118 extend substantially vertically between bottom surface 112 and recessed bottom surface 114.

Figure 6:
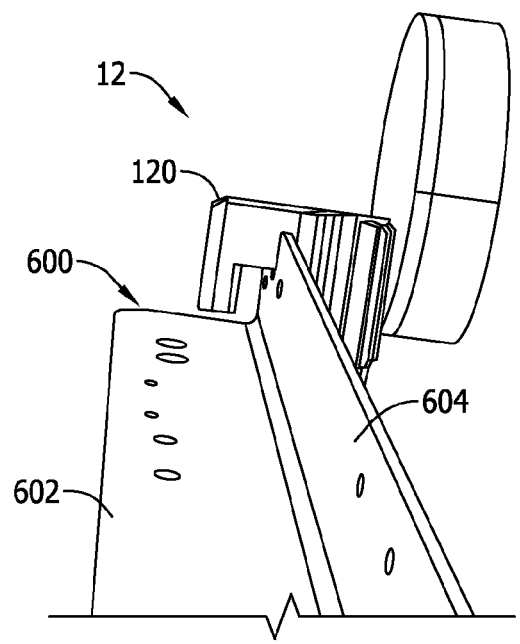
FIG. 6 is a perspective view of the tube hanger shown in FIGS. 1-5 coupled to a first frame type.
Figure 7:
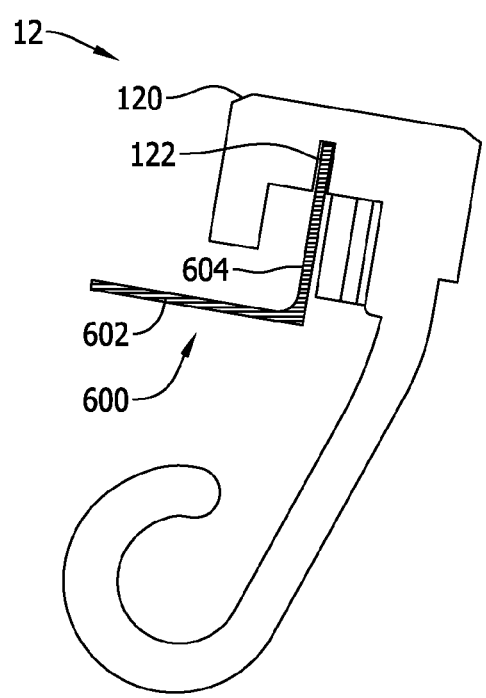
FIG. 7 is a side view of the tube hanger and the first frame type shown in FIG. 6.

FIG. 6 is a perspective view of tube hanger 12 coupled to a first frame type 600. FIG. 7 is a side view of tube hanger 12 and first frame type 600 (shown in FIG. 6). Referring to FIGS. 2-7, support coupling mechanism 104 includes a first attachment mechanism 120 defined within recessed bottom surface 114. First attachment mechanism 120 includes a first slot 122 defined within support coupling mechanism 104 via recessed bottom surface 114. First slot 122 has a first width W1. First attachment mechanism 120 is configured to be coupled to a first frame type 600. First slot 122 is sized and shaped to receive a mounting surface of first frame type 600. First width W1 is substantially the same as a width of first frame type 600, wherein first width W1 is approximately the same as or slightly larger than the width of first frame type 600, such that a friction fit is generated when first slot 122 is mounted on first frame type 600. First frame type 600 includes a minimum height requirement for first attachment mechanism 120 to be securely coupled thereto. In one implementation, first frame type 600 includes a mounting surface having a height between about one inch and two inches. In another implementation, first frame type 600 includes a mounting surface having a height of at least one inch. First frame type 600 may be coupled to an interior surface of a fuselage of the aircraft and is exposed and is available for coupling tube hanger to during manufacturing before interior cabin installation commences.

In the exemplary implementation, first frame type 600 is an L-shaped frame having a web 602 extending in a substantially horizontal direction and a mounting surface 604 coupled to web 602 and extending substantially vertically relative to web 602. Width W1 of first slot 122 is substantially the same or slightly larger as a width of mounting surface 604. Moreover, first slot 122 has a height that enables first attachment mechanism 120 to receive at least a portion of a height of mounting surface 604. The height of first slot 122 is sufficient to provide a secure mounting of support coupling mechanism 104 on first frame type 600.

Figure 8:
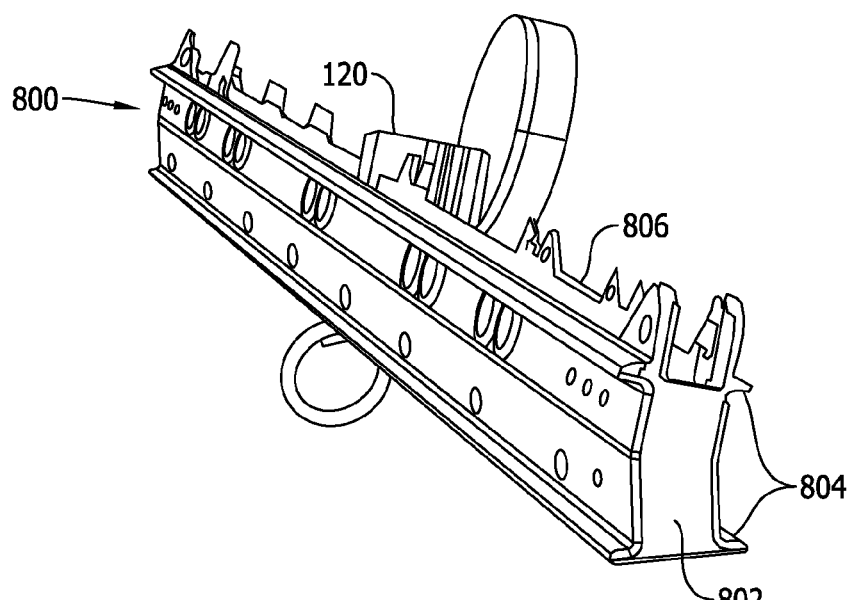
FIG. 8 is a perspective view of the tube hanger shown in FIGS. 1-5 coupled to a second frame type.
Figure 9:
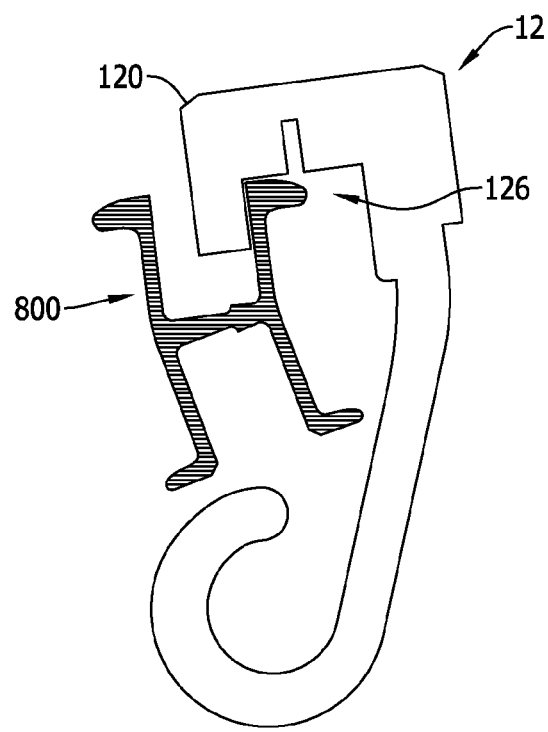
FIG. 9 is a side view of the tube hanger and the second frame type shown in FIG. 8.

FIG. 8 is a perspective view of tube hanger 12 coupled to a second frame type 800. FIG. 9 is a side view of tube hanger 12 and second frame type 800. Referring to FIGS. 2-5, 7, and 8, support coupling mechanism 104 includes a second attachment mechanism 124 defined within bottom surface 112. Second attachment mechanism 124 includes a second slot 126 defined by recessed bottom surface 114 and first and second recessed side surfaces 116 and 118. Second attachment mechanism 124 is configured to be coupled to a second frame type 800. Second slot 126 is sized and shaped to receive a mounting surface of second frame type 800. Second attachment mechanism 124 includes a second width W2 that is greater than the first width W1. The second width W2 is substantially the same as a width of second frame type 800. In one implementation, second frame type 800 includes a mounting surface having a height that is less than or equal to about ¼ inches. Second frame type 800 may be coupled to an interior surface of a fuselage of the aircraft and is exposed and is available for coupling tube hanger to during manufacturing before interior cabin installation commences.

In the exemplary implementation, second frame type 800 is an I-shaped frame that includes a web 802 extending in a substantially vertical direction, flanges 804 coupled to a top and bottom portion of web 802, and a mounting surface 806 coupled to and extending substantially vertically from top flange 804. Because mounting surface 806 has a height that is less than or equal to about ¼ inches, first attachment mechanism 120 is not able to securely couple to mounting surface. Thus, second attachment mechanism 124 enables coupling of tube hanger 12 to both top flange 804 and mounting surface 806. Width W2 of second slot 126 is substantially the same as or slightly larger than a width of top flange 804, enabling support coupling mechanism 104 to be coupled thereto. Additionally, first slot 122 is configured to receive mounting surface 806 of second frame type 800. Thus, second attachment mechanism 124 provides a second option for secure attachment of tube hanger 12 within an aircraft, depending on what type of frame is exposed at the particular stage of manufacturing.

Figure 10:
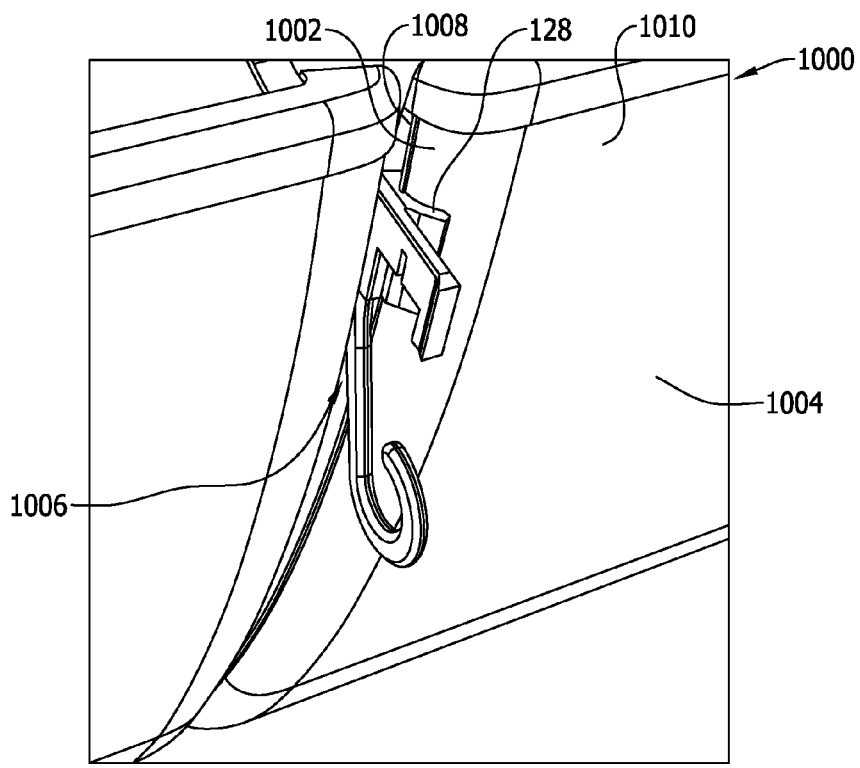
FIG. 10 is a perspective view of the tube hanger shown in FIGS. 1-5 coupled to a third frame type.
Figure 11:
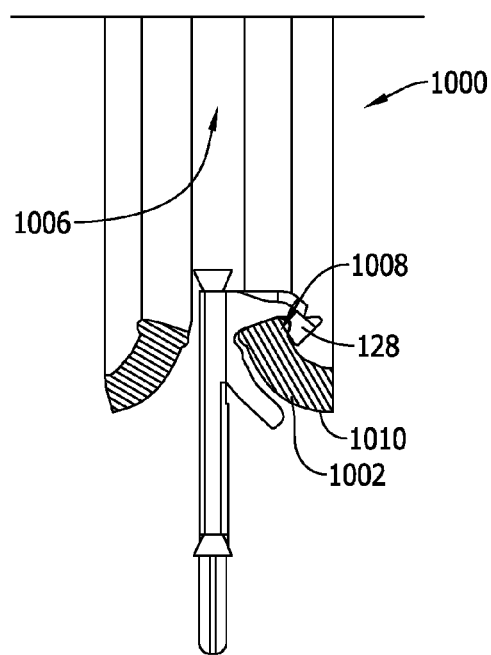
FIG. 11 is a top view of the tube hanger and the third frame type shown in FIG. 10.

FIG. 10 is a perspective view of tube hanger 12 coupled to a third frame type 1000. FIG. 11 is a top view of tube hanger 12 and third frame type 1000. Referring to FIGS. 2-5, 10, and 11, support coupling mechanism 104 includes a third attachment mechanism 128 extending from a side surface 130 of support coupling mechanism 104. Third attachment mechanism 128 is configured to be coupled to a third frame type 1000. Third attachment mechanism 128 includes a first arm 132 having a first end 134 extending from side surface 130, and a second end 136. Third attachment mechanism 128 also includes first coupling element 138 coupled to second end 136 of first arm 132 at a first angle, and a second arm 140 extending from support coupling mechanism 104 at a distance from first arm 132. The distance between first and second arms 132 and 140 defines a void 142 therebetween. Void 142 is sized and shaped to couple to third frame type 1000.

In the exemplary implementation, third frame type 1000 is an overhead stowage bin in the aircraft. More specifically, third frame type 1000 is a side edge 1002 of a door 1004 of a stowage bin. An opening 1006 is defined between two adjacent stowage bins when installed in an aircraft. Support coupling mechanism 104 is sized to fit within opening 1006 and third attachment mechanism 128 is configured to couple to door 1004 of the stowage bin. More specifically, third attachment mechanism 128 is configured to receive side edge 1002 within void 142 such that first and second arms 132 and 140 contact respective rear and front surfaces 1006 and 1008 of door 1004. Thus, third attachment mechanism 128 effectively clamps onto the stowage bin for mounting sampling tube 16 in the aircraft without causing damage to sampling tube 16, tube hanger 12, and/or the stowage bin. Third attachment mechanism 128 is typically used during later stages of manufacturing when aircraft frame components have been covered by walls and/or any other aircraft interior components.

Generally, tube hanger 12 is configured for at least temporary coupling to support structure 20, i.e., support coupling mechanism 104 is configured to be coupled to and uncoupled from support structure 20. Support coupling mechanism 104 may be configured for repeated coupling to and/or uncoupling from support structure 20 without significantly damaging support structure 20, support coupling mechanism 104, and/or tube hanger 12.

Tube hanger 12 is configured for use in an enclosed space (e.g., within an aircraft). Therefore, tube hanger 12 is generally configured to avoid harm to personnel, equipment, and the enclosed space. Tube hanger 12 is lightweight, compact, non-marring, and/or smooth. For example, tube hanger 12 is configured to avoid causing injury and/or damage if tube hanger 12 is dropped and/or dislodged from support structure 20. As another example, tube hanger 12 may be constructed without snags, protrusions, and/or sharp edges that could harm support structure 20, a person, and/or equipment.

Tube hanger 12 is generally constructed of materials selected for environmental resistance (e.g., exposure to temperature extremes, chemical solvents, and/or electrical hazards), durability, and flexibility (including elastic characteristics). Tube hanger 12 and components thereof (e.g., tube hook 100, suspension arm 106, and support coupling mechanism 104) may include spring elements and/or have spring characteristics. Tube hanger 12 may be manufactured using at least one of a polymer, a plastic, and a metal, and may include a durable, smooth finish. Alternatively, tube hanger 12 may be substantially composed of at least one of a polymer, a plastic and a metal. Suitable materials include, but are not limited to including, nylon, ABS plastic (acrylonitrile butadiene styrene), steel, iron alloys, and copper alloys. Tube hanger 12 may also include a soft, durable outer coating, e.g., the outer coating may be non-marring, elastic, conformable, and/or impact absorbing.

As shown in FIGS. 2-5, tube hanger 12 includes tube hook 100, support coupling mechanism 104, and suspension arm 106 spanning between tube hook 100 and support coupling mechanism 104. The components of tube hanger 12 form a unitary body (i.e., a one-piece structure) that simplifies installation and/or removal of tube hanger 12 from support structure 20 as well as engagement and/or disengagement of sampling tube 16. In the exemplary implementation, the unitary body is formed using 3D parametric CAD design and additive manufacturing. However, any known method of manufacturing may be used including, but not limited to, stamping, folding, rolling, forming, molding, extruding, and/or machining. Alternatively, the components forming tube hanger 12 may be manufactured as separate components that are coupled together using known techniques.

Tube hanger 12 may be visually distinct and may include tags, symbols, and/or coloration that are configured to make the device readily identifiable. In one implementation, support coupling mechanism 104 includes an internal RFID tag 144 (shown in FIG. 2) for use with tool tracking applications. Additionally, visual indications aid inspection of installation and removal of the tube hanger 12, and aid worker safety. Where tube hanger 12 may hang near equipment and/or personnel, the visual indication provides a warning of the presence of tube hanger 12. Hence, personnel are apt to avoid hitting themselves or equipment against tube hanger 12. Tube hanger 12 are visually distinct when distinctively colored, contrasting with nearby structures, striped, fluorescent, luminescent, luminous, and/or brightly colored (e.g., bright red, bright pink, bright yellow, bright green, bright blue, etc.).

Figure 12:
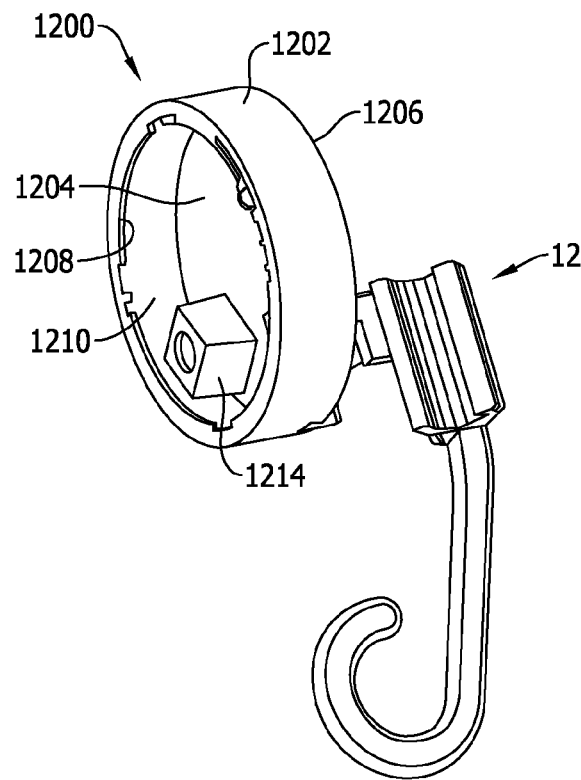
FIG. 12 is a perspective view of the tube hanger shown in FIGS. 1-5 including a smoke detector mount.
Figure 13:
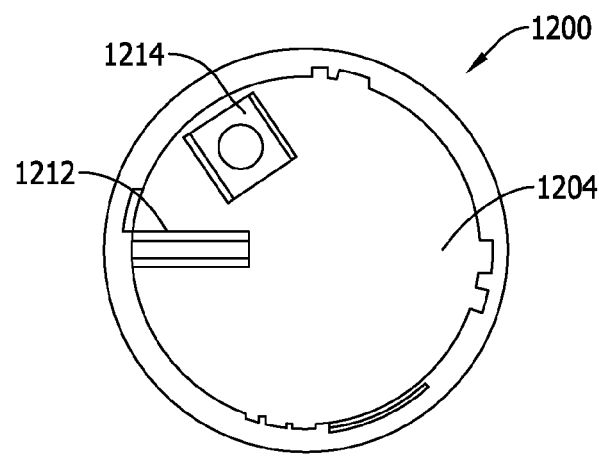
FIG. 13 is a side view of the smoke detector mount shown in FIG. 9.

FIG. 12 is a perspective view of tube hanger 12 (shown in FIGS. 1-5) including a smoke detector mount 1200. FIG. 13 is a side view of smoke detector mount 1200.

Smoke detector mount 1200 includes a cylindrical shell 1202 having a sidewall 1204 covering a first end 1206 and is open at a second end 1208, forming a cavity 1210 therein. A slot 1212 is defined through sidewall 1204 for receiving tube hanger 12. More specifically, slot 1212 is configured to receive one of first attachment mechanism 120 or second attachment mechanism 124, which is secured to sidewall 1204 with first or second slot 122 or 126. Smoke detector mount 1200 also includes a magnet housing 1214 coupled to an inner surface of sidewall 1204 within cavity 1210 that is configured to receive and secure a magnet.

Smoke detector mount 1200 is sized and shaped to be coupled to a Wi-Fi smoke detector onboard an aircraft. More specifically, cavity 1210 of smoke detector mount 1200 is configured to be positioned over a Wi-Fi smoke detector for supporting sampling tube 16. A magnet may be placed within magnet housing 1214 to create a magnetic attraction between smoke detector mount 1200 and a magnet included within the Wi-Fi smoke detector, improving the strength of the attachment of smoke detector mount 1200.

The above described embodiments of tube hangers for VESDA systems provide tube installation in multiple locations of an aircraft based on a present stage of manufacturing of the aircraft. More specifically, embodiments described herein provide a tube hanger that includes a first attachment mechanism configured to be coupled to a first frame type, a second attachment mechanism configured to be coupled to a second frame type, and a third attachment mechanism configured to be coupled to a third frame type. The tube hangers described herein enable personnel working in the aircraft to easily move the tube hanger to a different position as the manufacturing process proceeds and different frame types for attachment thereto become covered up or exposed. The tube hangers reduce time needed for installation of the sampling tube. The embodiments further reduce an amount of time spent by a safety/fire department tracking down the correct personnel to fix issues that are found with the installation as well as reduce re-installation that has to take place when the tube is not installed correctly. Moreover, the embodiments facilitate reducing the time a mechanic has to spend relocating the tubing if it is in the way of a job. The tube hanger further facilitates preventing the sampling tube from being placed on the floor, which may result in making the VESDA system not perform optimally, damage to the sampling tube, and/or damage to the aircraft from the sampling tube lying across the top of seats or the floor. By enabling personnel to easily and correctly install and reposition the sampling tubes during the manufacturing process, the tube hangers described herein improve personnel and aircraft safety.

Exemplary embodiments of tube hangers and systems for very early smoke detection are not limited to the specific embodiments described herein, but rather, components of systems and/or steps of the methods may be utilized independently and separately from other components and/or steps described herein. For example, the methods may also be used in combination with other non-conventional tube hangers, and are not limited to practice with only the systems and methods as described herein. Rather, the exemplary embodiment can be implemented and utilized in connection with many other applications, equipment, and systems that may benefit from increased efficiency, reduced operational cost, and reduced capital expenditure.

An exemplary technical effect of the tube hangers and systems for very early smoke detection described herein includes at least one of: (a) coupling a tube to a first vehicle frame type during a first stage of manufacturing; (b) coupling the tube to a second frame type during a second stage of manufacturing of the vehicle; (c) coupling the tube to a third frame type during a third stage of manufacturing of the vehicle; (d) reducing time needed for installation of the sampling tube in the vehicle; (e) reducing an amount of time spent by a safety/fire department tracking down the correct personnel to fix issues that are found with the installation; (f) reducing re-installation that has to take place when the tube is not installed correctly; (g) reducing the time a mechanic has to spend relocating the tubing if it is in the way of a job; (h) preventing the sampling tube from being placed on the floor, which may result in making the VESDA system not perform optimally, damage to the sampling tube, and/or damage to the aircraft from the sampling tube laying across the top of seats or the floor; and (i) improving personnel and aircraft safety.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A tube hanger for a very early smoke detection system, said tube hanger comprising:
   a tube hook configured to receive a tube;
   a suspension arm comprising a first end extending from said tube hook and a second end;
   a support coupling mechanism extending from said second end of said suspension arm, said support coupling mechanism comprising:
      a first attachment mechanism configured to be coupled to a first frame type; and
      a second attachment mechanism configured to be coupled to a second frame type; and
   a third attachment mechanism extending from said support coupling mechanism and configured to be coupled to a third frame type.

2. The tube hanger of claim 1, wherein said support coupling mechanism comprises a bottom surface, at least a portion of said bottom surface is a recessed bottom surface that is recessed within said support coupling mechanism.

3. The tube hanger of claim 2, wherein said first attachment mechanism comprises a first slot defined within said support coupling mechanism via said recessed bottom surface, said first slot having a first width.

4. The tube hanger of claim 3, wherein said first slot is sized and shaped to receive the first frame type.

5. The tube hanger of claim 3, wherein the first width is substantially the same as a width of the first frame type.

6. The tube hanger of claim 3, wherein said second attachment mechanism comprises a second slot defined within said support coupling mechanism by said recessed bottom surface and first and second recessed side surfaces, said second attachment mechanism having a second width that is greater than the first width.

7. The tube hanger of claim 6, wherein said second slot is sized and shaped to receive the second frame type.

8. The tube hanger of claim 6, wherein the second width is substantially the same as a width of the second frame type.

9. The tube hanger of claim 1, wherein said third attachment mechanism extends from a side surface of said support coupling mechanism.

10. The tube hanger of claim 1, wherein said third attachment mechanism comprises:
    a first arm having a first end extending from said support coupling mechanism and a second end;
    a first coupling element extending from the second end of said first arm at a first angle; and
    a second arm extending from said support coupling mechanism at a distance from said first arm to define a void therebetween, the void sized and shaped to couple to the third frame type.

11. A tube hanger for a very early smoke detection system, said tube hanger comprising:
    a tube hook configured to receive a tube;
    a support coupling mechanism comprising:
       a first attachment mechanism configured to be coupled to a first frame type during a first stage of manufacturing of a vehicle; and
       a second attachment mechanism configured to be coupled to a second frame type during a second stage of manufacturing of the vehicle;
    a third attachment mechanism extending from said support coupling mechanism and configured to be coupled to a third frame type during a third stage of manufacturing of the vehicle; and
    a suspension arm spanning between said tube hook and said support coupling mechanism.

12. The tube hanger of claim 11, wherein said first attachment mechanism defines a first slot therein configured to receive the first frame type including a mounting face having a height between about one inch and two inches.

13. The tube hanger of claim 11, wherein said second attachment mechanism defines a second slot therein configured to receive the second frame type including a first mounting face having a width less than or equal to the second width of said second attachment mechanism.

14. The tube hanger of claim 13, wherein the second frame type further includes a second mounting face positioned on top of the first mounting surface and having a height less than or equal to about ¼ inches, wherein said first attachment mechanism and said second attachment mechanism simultaneously couple to respective first and second mounting faces.

15. The tube hanger of claim 11, further comprising a smoke detector mount comprising a slot defined therethrough for coupling to one of said first attachment mechanism or said second attachment mechanism.

16. The tube hanger of claim 15, wherein said smoke detector mount is sized and shaped to be coupled to a Wifi smoke detector.

17. The tube hanger of claim 11, wherein said support coupling mechanism further comprises an internal RFID tag for tool tracking applications.

18. A very early smoke detection system comprising:
    a monitoring device;
    a sampling tube coupled to said monitoring device; and
    a tube hanger for mounting said sampling tube in an environment, said tube hanger comprising:
       a tube hook configured to receive said sampling tube;
       a suspension arm comprising a first end extending from said tube hook and a second end;
       a support coupling mechanism extending from said second end of said suspension arm, said support coupling mechanism comprising:
          a first attachment mechanism configured to be coupled to a first frame type; and
          a second attachment mechanism configured to be coupled to a second frame type; and
       a third attachment mechanism coupled to said support coupling mechanism and configured to be coupled to a third frame type.

19. The system of claim 18, wherein said support coupling mechanism comprises a bottom surface, at least a portion of said bottom surface is a recessed bottom surface that is recessed within said support coupling mechanism.

20. The tube hanger of claim 19, wherein:
    said first attachment mechanism comprises a first slot defined within said support coupling mechanism via said recessed bottom surface, said first slot having a first width; and
    said second attachment mechanism comprises a second slot defined within said support coupling mechanism by said recessed bottom surface and first and second recessed side surfaces, said second attachment mechanism having a second width that is greater than the first width.

* * * * *